United States Patent [19]

Muhlbauer

[11] Patent Number: 4,537,303
[45] Date of Patent: Aug. 27, 1985

[54] DEVICE AND METHOD FOR MIXING LIQUID AND POWDERY COMPONENTS, PARTICULARLY FOR DENTAL PURPOSES

[76] Inventor: Ernst Muhlbauer, Dorpfeldstieg 3, 2000 Hamburg 52, Fed. Rep. of Germany

[21] Appl. No.: 557,472

[22] Filed: Dec. 2, 1983

[30] Foreign Application Priority Data

Feb. 4, 1983 [DE] Fed. Rep. of Germany ....... 3303838

[51] Int. Cl.³ .............................................. B65D 25/08
[52] U.S. Cl. .................................... 206/219; 206/220
[58] Field of Search ................................ 206/219, 220

[56] References Cited

U.S. PATENT DOCUMENTS

| 3,454,177 | 7/1969 | Bloom. | |
| 4,182,447 | 1/1980 | Kay | 206/220 |
| 4,291,799 | 9/1981 | Bower, Jr. | 206/219 |
| 4,306,651 | 12/1981 | Muhlbauer | 206/220 |
| 4,312,473 | 1/1982 | Hoeller | 206/219 |

FOREIGN PATENT DOCUMENTS

| 1566557 | 2/1971 | Fed. Rep. of Germany. |
| 1960074 | 6/1971 | Fed. Rep. of Germany. |
| 1144883 | 10/1957 | France. |

Primary Examiner—Joseph Man-Fu Moy
Attorney, Agent, or Firm—Prutzman, Kalb, Chilton & Alix

[57] ABSTRACT

A portion package assembly of dental amalgam components and a method of mixing in a vibration dental mixing capsule is disclosed comprising a first portion package having a foil pocket containing a predetermined amount of powdery dental component with the foil pocket being comprised of material adapted to rupture in a dental mixing capsule during vibration and having a specific gravity of at least several times less than the specific gravity of the powdery dental component and a second portion package having a foil pocket containing a predetermined amount of liquid dental component coordinated to the predetermined amount of powdery component with the foil pocket being comprised of material adapted to rupture in the mixing capsule during vibration mixing.

16 Claims, 14 Drawing Figures

DEVICE AND METHOD FOR MIXING LIQUID AND POWDERY COMPONENTS, PARTICULARLY FOR DENTAL PURPOSES

BACKGROUND AND SUMMARY OF THE INVENTION

This invention relates to a method of mixing a liquid and a powdery component by vibration of a mixing chamber containing the components, particularly for dental purposes, in which the liquid component, tightly enclosed in a foil bag, is inserted in the mixing chamber and exposed to the mixing vibration, the strength of the foil bag being predetermined such that it releases its contents under the action of the mixing vibration. The invention also relates to a mixing capsule and a portion package for practicing the method.

In U.S. Pat. No. 4,306,651 to the present applicant which disclosure is incorporated herein by reference, a multicomponent capsule for dental purposes is shown wherein one component is freely contained in the mixing chamber of the capsule and the other component is contained in a foil bag and thereby separated from the one component until the foil bag is destroyed by the mixing vibration. Obviously it is sufficient to enclose merely one component in a bag so as to ensure chemical separation during the storage period. The use of a multi-component capsule for storage and for a single mixing operation involves a certain expenditure, which can be avoided where the dentist places silver powder as well as, by means of a dosing apparatus, a corresponding quantity of mercury into a mixing capsule for multiple use, closes the capsule and subsequently mixes the components in a vibration apparatus. While this method is less expensive, inexact dosages may result more readily than with a mechanical predosing, and the physician is exposed to the immediate influence of the mercury.

The present invention concerns the problem of combining the simplicity of the method as known from the use of disposable capsules with the low expenditure involved in the repeated use of the capsule.

The solution according to the invention resides in the fact that the powdery component is also enclosed in a separate foil bag which is exposed to vibration and opens under the action of the mixing vibration, with the foil bag consisting of a material having a specific gravity several times lower than that of the powdery component.

The enclosure of both components in respective foil bags permits their optional use, irrespective of whether they are supplied a priori in a disposable capsule or whether they will be inserted by the dentist into a mixing capsule to be used, if necessary, several times. Furthermore, it permits an easy and simple dosing by inserting in each case such a number of foil bags with the components into a mixing capsule as it corresponds to the desired amalgam amount.

It could not be expected that powder would liberate itself sufficiently completely from a foil bag which opens under the mixing vibration since it cannot be expected even of the liquid component under certain conditions. For example, there is the possibility that mercury will not be discharged completely from a sealed metal foil bag as disclosed in U.S. Pat. No. 4,182,447. If the complete emptying of the foil bag appears not to be ensured even with liquids under certain conditions, then this could much less be expected as regards the storage of a powder in a foil bag. It is more surprising that the complete discharge of the powdery component is achieved if, according to the present invention, the specific gravity of the bag material is several times lower than that of the powder. It may be assumed that this effect is due to the fact that, in accordance with the law that "force equals mass times acceleration", the forces exerted under the vigorous vibration accelerations on the substances contained in the capsule are considerably smaller regarding the specifically lighter bag material than regarding the powder particles so that the latter are separated from each other by the very different forces acting on them. It may also be of importance in this connection that under vibration conditions the powder does not behave as a solid but similar to a liquid. This is due to the fact that the powder particles get into a relative motion with respect to each other, whereby air layers are enclosed between them which terminate the solid connection and put the powder on the whole into a so-called fluidized state, which is known and being used in another technical field, namely that of the mechanical conveying and handling of powdery material.

It can easily be determined by experiments by how many times the specific gravity of the powder must be greater than that of the bag material. There is to be achieved a density ratio, relative to the solid powder material, of at least 5 and preferably of more than 8.

The invention relates furthermore to a mixing capsule for carrying out the stated method of the vibration mixing of several components contained therein, particularly for dental purposes. The mixing capsule contains in a mixing chamber a liquid component tightly enclosed in a foil bag for releasing said component under the action of mixing vibration and a powdery component. The powdery component is contained in a separate foil bag opening under the action of the mixing vibration with the foil bag consisting of a material having a specific gravity several times less than that of the powdery component by a factor of at least 5 and preferably more than 8.

Finally, this invention relates to a portion package for silver powder or the like powdery dental material intended for vibration mixing in a dental mixing capsule. In the package, the powder is enclosed in a foil bag, the material of which is specifically several times lighter than the powder and the strength of which is predetermined such that it opens under the action of the mixing vibration in the mixing chamber of the dental mixing capsule.

The enclosure of the powder, particularly of the silver powder, in a foil bag has the great advantage that the portion size can be predetermined with great exactness. This advantage exists also if the powder is present in a briquetted form. It is known to make the silver powder available to the dentist in the form of compressed tablets, which disintegrate to powder under the action of mixing vibration and are industrially adjusted to a specific weight portion. Since these tablets are rubbing against each other during transport and use, for instance when taking out individual tablets, there occurs a constant loss in weight by abrasion which may lead to an error in the weight ratios in the amalgam preparation. Such loss by abrasion is prevented by the enclosure of the silver in foil bags.

According to a further feature of the present invention, portion packages of the dental material components to be used together can be connected to each other. This presents not only the advantage that the use is simplified since in each case only one portion package with both components needs to be inserted in the mixing capsule but also the portioning becomes more reliable since no mistakes can occur in the coordination of component amounts suited to each other. Additionally, several portion packages can be inserted in the mixing capsule at a time, such as for a large tooth filling there is required an amalgam amount greater than that provided by one portion package.

The connection of the two individual portion packages to a common portion package can be achieved in a simple way, e.g., by adhesion bonding. According to another feature of the present invention, the connection between the individual portion packages is obtained in that at least one foil is involved in the formation of both portion packages. Preferably, even both portion packages are formed integrally by a pair of foils, which are welded together in forming two separate portion pockets.

According to a further embodiment of this invention, two cover foils are welded together with a central foil, in forming two portion pockets situated on both sides of the central foil.

The destruction of the foil bag containing the liquid component is facilitated by the powdery component being packed in a foil bag and combined as a unit with the liquid bag, since the entire powder material substantially simultaneously exerts impact on the liquid bag and thus a stronger effect thereon than simply a powder distributed in the entire space.

There may be provided devices which improve the opening of the foils under the action of the mixing vibration and/or the mixing effect, for example a pestle, which may also be contained in the portion package, or edges or prongs projecting inwards from the wall of the mixing chamber.

If a capsule is to be used repeatedly for the preparation of amalgam, it has to be cleaned between the individual applications or at least from time to time. Furthermore, it has to be considered a disadvantage that the prepared mixture must be taken out of the capsule in a relatively complicated way, in which respect also the remainders of the consumed package, likewise contained in the capsule, can be inconvenient. Such disadvantage can be avoided in accordance with the present invention in that the package foil, destructible by the action of the mixing vibration, together with the portion chambers separated therefrom and including the dental material components, is enclosed by a package casing not destructible by the action of the mixing vibration.

After the mixing process, the mixed material is not contained in a free form within the mixing chamber of the mixing capsule but is still enclosed by the foil bag, wherein merely the inner separating foil has been destroyed. One can therefore simply take the closed portion package out of the mixing capsule, tear it open and take out the mixture by a spatula or squeeze it out between two fingers. Thereby the removal of the mixture is substantially simplified, and it is achieved without special measures that the mixture remains hygienic.

The arrangement of the package foil destructible by the mixing vibration with respect to the nondestructible packaging casing can be different. In one advantageous embodiment there are provided for example two foil bags, one of which freely encloses as a convering foil bag the first dental material component as well as the destructible foil bag containing the second dental material component. In accordance with another expedient embodiment, it is provided that two foils, together forming the covering foil bag, are welded together on both sides of the destructible foil either to the latter or to each other.

After mixing, the outer package casing which is not destructible by the mixing vibration forms a container for the mixed dental material. In order that the container can be handled more easily, it can be formed according to the invention as a semi-flexible, cup-like package portion. The term semi-flexible is to mean that the container retains its cup shape in a more or less deformed state, even if it is held between the fingers in order to be emptied. Its cup shape facilitates the removal of the mixed material.

Additionally, it may be provided according to the present invention that the package casing is provided with an opening device. An opening device is understood to mean those elements or formations which enable or facilitate the opening process. This includes, for example, gripping lugs projecting outwards from the portions forming the actual package casing so as to allow, for the purpose of opening, a gripping thereof and the exertion of a force. Furthermore, this includes ideal tearing points and notches in the welding edge at which the opening tear may be started.

The portion package according to the present invention can enclose the dental material components without a substantial empty space so that the mixing forces created upon the impact of the portion package during the mixing vibration at the ends of the mixing capsule will be transferred, without being damped, onto the dental material components to be mixed. This applies particularly if a flexible material is used for the nondestructible package casing, which completely transmits the forces to the dental material. Instead of this, it may, however, also be provided that the portion package includes a certain empty space permitting a certain vortexing. This applies particularly if the package casing consists wholly or partially of a semi-flexible or a stiffer material.

It may also be expedient that the portion package contains a pestle, i.e., a body of, for instance, glass, ceramics, synthetic material, which, due to its movement within the portion package, caused by the mixing vibration, assists in the mixing of the components.

It is not necessary that the two component bags are inserted in a mixing capsule only at the dentist and immediately prior to use, but the invention rather presents also the advantage that the filling of the capsule becomes independent of the dosing and encasing of the components. Finally, there is achieved the advantage that it is not necessary to tightly close the capsule, even if the latter is intended for long-term storage, since the components in their bag packages can be sufficiently sealed against atmospheric influences and it can be prevented that, due to evaporation, they emit poisonous influences into the atmosphere.

The foil packages may be provided with imprints, i.e., with statements as required under the drug law, such as the name of the manufacturer, weight, durability, data of filling, specification of the materials, etc. The individual foil packages can be lined up as double packages or individually within a strip of similar packages and can be separable from each other and, if necessary, from the strip section provided with the information by perforation or predetermined breaking points, respectively.

The invention presents considerable price advantages over the known disposable capsules, which mostly have to be additionally prepared for mixture by turning, pressing or screwing. The encasing of the amalgam powder in foil bags can also be advantageous over the processing in the form of tablets since the latter first have to be compressed, which involves costs. Moreover, it can be disadvantageous for some amalgam powders to be compressed to tablets. Finally, the abrasion of the tablets may lead to differences in weight. Compared with the use of automatic mixers, the invention involves the advantages of a greater exactness, that amalgams of any kind can be used, that no maintenance of the apparatuses is required, and that the dentist is not exposed to mercury vapor.

The portion package of the components to be mixed can be inserted in the mixing capsule at any point of the chain between production, storage and use.

In the context of the invention both the mixing capsule and the vibration mixers used for dental purposes can be considered to be known. The mixing capsules are elongated containers closed by a removable lid and having a length in the order of magnitude of 3 cm and a diameter in the order of magnitude of 1 cm. The mixers are formed such that the mixing capsules inserted therein can be reciprocated in their longitudinal direction at a frequency of, e.g., 300 Hz so that the material contained in the interior of the capsule (mixing chamber) is flung to and fro between the end walls of the mixing chamber. The volume of the material amounts to only a very small part of the volume of the mixing chamber. Typical amalgam portions as they are prepared by the dentist in one mixing operation lie between 0.5 g and 1 g.

With respect to foil materials, there are particularly suitable synthetic materials, e.g., a polyethylene foil of a thickness in the order of magnitude of 0.05 mm.

BRIEF DESCRIPTION OF THE DRAWINGS

In the following the invention will be described in greater detail by reference to the drawings, which schematically illustrate advantageous embodiments of the invention. In the drawings there are shown in.

DESCRIPTION OF THE PREFERRED EMBODIMENT

Figure 1:
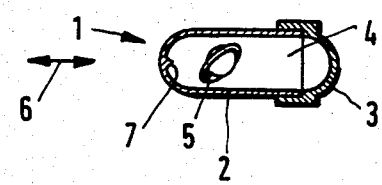
FIG. 1 a longitudinal section through a mixing capsule in about nature size.

The mixing capsule 1 consits of a container portion 2 and a removable lid 3 which is fittingly arranged thereon and can, if necessary, be closed again, said elements together enclosing the mixing chamber 4, in which a portion package 5 is disposed comprising respective portion pockets for matching amounts of mercury and silver powder. By vibration of the capsule in a mixer (not shown) in the direction of the arrow 6 the portion package 5 is alternatingly caused to vigorously impact on both front surfaces of the mixing chamber 4, during which the packing casing is tearing up, releases the contents, whereupon the mixing of the components can take place. In order to facilitate the tearing up and, if necessary, also the mixing process, one front surface comprises, at 7, a pointed projection extending into the mixing chamber.

Figure 2:
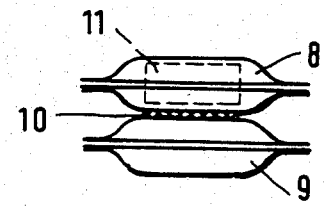
FIG. 2 a portion package with two individual portion packages connected by gluing.

According to FIG. 2, the portion package consists of two individual packages 8, 9 for silver and mercury, respectively, which are connected to each other by adhesion bonding 10. The silver powder can be contained therein in the form of powder or also, as shown at 11 by dotted lines, in the form of a briquetted tablet.

Figure 3:
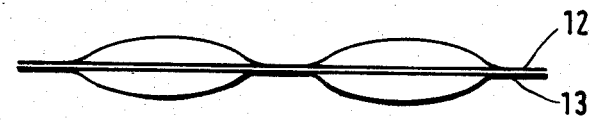
FIGS. 3 and 4 a side elevation and a top view of a portion package connected to form one piece.
Figure 4:
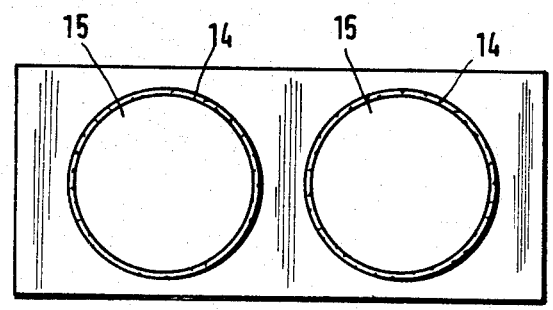

The second embodiment of the portion package according to FIGS. 3, 4 consists of two foils 12, 13, which are welded together in closed circles 14 to form tight portion pockets 15 for respectively receiving the silver powder and the mercury or other dental materials.

Figure 5:
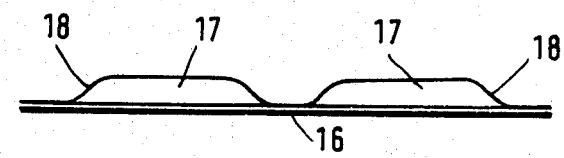
FIG. 5 a third embodiment.

In the third embodiment according to FIG. 5 only one foil 16 is formed to be continuous, whereas the portion pockets 17 thereon are formed by individually cut-out foil pieces 18 and a welding corresponding to FIG. 4.

Figure 6:
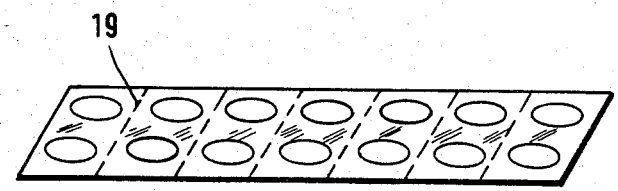
FIG. 6 a package strip comprising several double-portion packages separable from each other.

The portion packages according to FIGS. 3 and 5 can be kept in stock in the form of package strips according to FIG. 6, wherein the portion packages, each of which consisting of two individual packages for the two components, can be easily separated from each other by means of a perforation 19.

Figure 7:
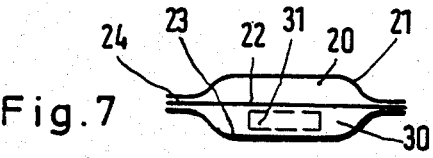
FIG. 7 a fourth embodiment.

In the fourth embodiment according to FIG. 7 two covering foils 21, 23 are circumferentially tightly welded in the area 24 to a central foil 22 in forming two portion pockets 20, 30. At least of the three foils are designed such that they become destroyed under the action of the mixing vibration and will release the contents. In FIG. 7 it is moreover shown that the portion package can comprise a pestle 31, for instance an inert plastic or glass piece in one of the portion pockets.

Figure 8:
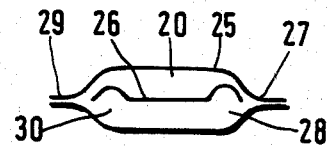
FIG. 8 a fifth embodiment of the portion package according to the invention, on an enlarged scale.

A fifth embodiment, similar to the embodiment according to FIG. 7, is shown in FIG. 8, with the difference that the central foil 26 is welded separately to the covering foil 25 at 27, while the other covering foil 28 is welded to the covering foil 25 at a distance from the welding seam 27 at 29. All welding seams are effected circumferentially so that the pockets 20, 30 are completely closed. The spacing of the welding seams 27 and 29 presents the advantage that they can be effected separately as to time and space.

Of course, the portion packages according to FIG. 2 or 7 or 8 can also be combined in a plurality thereof to package strips according to FIG. 6 so as to be separable from each other.

It is, of course, not necessary that in each portion package all foils serving for its formation are destructible under the action of the mixing vibration, but it is sufficient if in each case one foil used in the formation of each portion package is destructible. In many cases it is also sufficient if only one of these foils has a specific gravity several times lower than that of the powder component, even though expediently both foils used for forming the portion pockets provided for receiving the powder should comply with this requirement.

Figure 9:
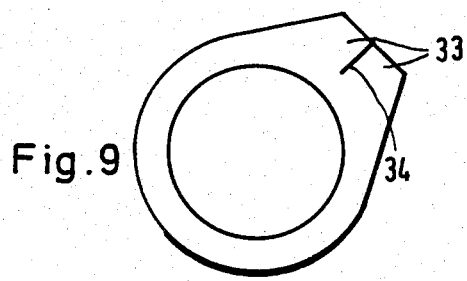
FIG. 9 a top view of a sixth embodiment of the portion package.
Figure 10:
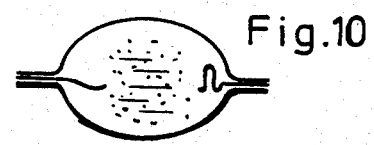
FIG. 10 a section, corresponding to FIG. 7, through the sixth embodiment of the package after mixture.

According to a sixth embodiment, which may be described likewise by reference to FIGS. 7 and 8, the covering foils 21 and 23 or 25 and 28, respectively, are together forming a package casing not destructible by the mixing vibration, while the central foil separating the portion pockets 20, 30 is made such that it is tearing up under the action of the mixing vibration, whereby, in accordance with FIG. 10, the two components can get together and are being mixed by the vibration. The welding seam can form, according to FIG. 9, two adjacent, outwardly projecting lugs 33, between which a slot or a notch 34 is provided. By pulling the lugs 33 in different directions, it is possible, starting from the notch 34, to tear up the bag after mixture in order to enable the removal of the contents.

Figure 11:
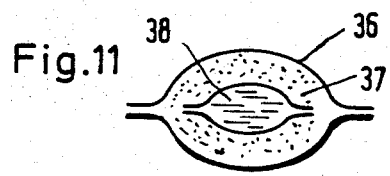
FIG. 11 a seventh embodiment with two bags, one disposed within the other.
Figure 12:
FIG. 12 the embodiment according to FIG. 6 after completion of the mixing operation.

In the seventh embodiment according to FIGS. 11 and 12 there is, apart from the silver powder 37, freely housed in the package casing 36, consisting of two foils welded together and not being destructible by mixing vibration, also a second package bag 38, which consists of the foil destructible by the mixing vibration and containing the mercury. During the mixing vibration, the bag 38 according to FIG. 12 is being destroyed so that the two components can get into contact.

Figure 13:
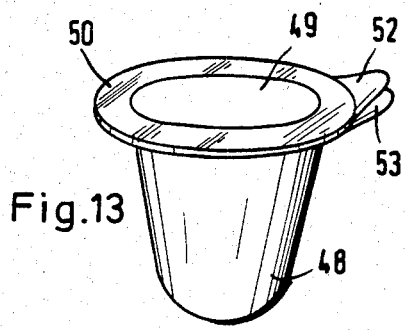
FIGS. 13 and 14 a perspective illustration and a sectional view of an eighth embodiment.
Figure 14:
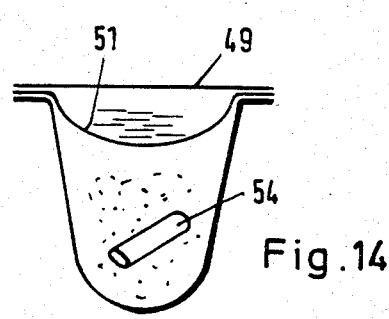

The foils of which the package casing consists in FIGS. 7 to 12 can be soft so that they do not tend to assume a specific configuration. After opening, the contents may be squeezed out of them. However, it is also possible instead of this that one of the two encasing foils is more rigid so as to form, after separation of the other encasing foil and, if necessary, of the separating foil, a dish or cup-shaped container, of which the mixed material can more easily be removed. In that case the opening devices are expediently formed such that it is possible to pull off one encasing foil like a lid, along the correspondingly weaker welding seam, from the edge of the other encasing foil which is formed as a dish or cup. The embodiment according to FIGS. 13 and 14 likewise follows that principle, wherein the markedly cup-shaped portion 48 of the package encasing is relatively rigid, while the covering foil 49, which is welded onto the rim of the cup portion 48 along the welding seam 50 in enclosing the separating foil 51, can be flat. The covering foil 49 and the cup portion 48 are provided at their rim with lug-like projections 52, 53, which can be gripped so as to enable a pulling off of the covering foil from the rim of the cup portion 48. In this connection the arrangement can be such that the separating foil 51 (in deviation from the illustration) is connected exclusively to the covering foil 49 or that the common welding seam of all three foils is weakest between the separating foil 51 and the rim of the cup portion 48 so that, when pulling off the covering foil 49, there will be simultaneously separated also the remainders of the separating foil from the cup portion 48.

The cup portion 48 can be made rather large with respect to the volume of the components to be mixed, so that there remains a gas-filled space, in which the components to be mixed can be hurled around with a mixing-improving effect when the package hits upon the ends of the mixing capsule. For improving the mixing effect, a pestle 54 can be additionally inserted. If reference is made in the claims to the cup shape, this is to include also similar forms, such as the dish shape in accordance with FIG. 7.

In the sixth to eighth embodiments, too, the foil which is destructible by the mixing vibration has expediently likewise a specific gravity several times lower than that of the powdery dental material, although these embodiments can be used also with materials having a specific gravity in the same order or even lower than that of the foil, for instance with the components or fillers for synthetic resinous dental materials.

I claim:

1. A method of mixing a dental amalgam in a vibration mixing chamber comprising the steps of:
   providing a predetermined amount of liquid dental component tightly enclosed in a first rupturable foil pocket of sufficient strength to rupture and thereby release the said predetermined amount of liquid dental component from the said first pocket upon the action of a mixing vibration,
   providing a predetermined amount of powdery dental component enclosed in a second rupturable foil pocket of sufficient strength to rupture and thereby release the said predetermined amount of powdery dental component from the said second pocket upon the action of a mixing vibration and comprised of a material having a specific gravity at least five times less than said powdery dental component, said predetermined amount of powdery dental component being coordinated to said predetermined amount of liquid dental component for forming a dental amalgam of fixed predetermined proportions of said liquid dental component and said powdery dental component,
   vibration mixing the first and second foil pockets in a vibration mixing chamber to rupture the foil pockets and admix the said predetermined amounts of the liquid and powdery dental components to form a dental amalgam of said fixed predetermined proportions of said liquid dental component and powdery dental component.

2. A dental vibration mixing capsule for vibration mixing a dental amalgam comprising,
   a capsule housing having a fully closed mixing chamber and adapted for vibratory mixing motion,
   a first package portion having a foil pocket containing a predetermined amount of powdery dental component, said foil pocket being comprised of a foil material adapted to rupture and discharge said predetermined amount of the powdery dental component in said mixing chamber during vibration mixing and the foil having a specific gravity at least five times less than the specific gravity of the powdery dental component, said first package portion being disposed in said mixing chamber, and
   a second package portion having a foil pocket containing a predetermined amount of liquid dental component coordinated to said predetermined amount of powdery component to form a dental amalgam of fixed predetermined proportions of said liquid dental component and said powdery dental component, said foil pocket being comprised of foil material adapted to rupture and discharge said predetermined amount of the liquid dental component in said mixing chamber during vibration mixing, said second package portion being disposed in said mixing chamber whereby said predetermined portion of the powdery component is separated from said liquid dental component during storage and said predetermined portion of the powdery dental component admixes with said predetermined portion of the liquid dental component to form an amalgam of said fixed predetermined proportions of said liquid dental component and said powdery dental component during mixing vibration of said capsule housing.

3. A portion package for a powdery dental component of a dental amalgam of said powdery dental component and a liquid dental component for vibration mixing of said components in a dental mixing capsule comprising, a predetermined amount of the said powdery dental component for forming a dental amalgam of fixed predetermined proportions of said powdery dental component and the said liquid dental component, and a foil bag enclosing said powdery dental component, said foil bag being of sufficient strength to rupture and thereby discharge said predetermined amount of said powdery dental component during vibration mixing in a dental mixing capsule and being comprised of a material having a specific gravity at least five times less than the specific gravity of said powdery component whereby said foil bag ruptures under the vibratory mixing in a dental mixing capsule and discharges said predetermined amount of said powdery dental component.

4. A dental material package assembly of dental material components for vibration mixing in a dental mixing capsule comprising, a first package portion enclosing a predetermined amount of a first powdery dental component, the first package portion being formed by a foil material having a specific gravity at least five times less than the specific gravity of said first powdery component, a second package portion of foil material enclosing a predetermined amount of a second liquid dental component coordinated to said predetermined amount of said first powdery dental component for forming a dental amalgam of fixed predetermined proportions of said liquid dental component and said powdery dental component, said second package portion being connected to said first package portion, and said first and second package portions being formed at least in part by a rupturable foil adapted to rupture by mixing vibration in a mixing capsule to release said predetermined amounts of said powdery dental component and said liquid dental component to form a dental amalgam of said fixed predetermined proportions of said liquid dental component and said powdery dental component during vibration mixing of the mixing capsule.

5. The package assembly of claim 4 wherein said first package portion is connected to said second package portion by adhesion bonding.

6. The package assembly of claim 4 wherein said first and second package portions are formed from at least one foil.

7. The package assembly of claim 6 wherein said first and second package portions are formed integrally by a pair of foils welded together to form two separate portion pockets.

8. The package assembly of claim 6 wherein two covering foils are welded to a central foil to form two portion pockets disposed on both sides of said central foil.

9. A package assembly according to claim 4 comprising a pestle contained therein.

10. The capsule according to claim 2 wherein the powdery dental component is in the form of a powdery briquette.

11. The package according to claim 3 wherein the powdery dental component is in the form of a powdery briquette.

12. The package according to claim 4 wherein the first component is a powder in the form of a briquette.

13. The device of claim 2 wherein the specific gravity of said foil pocket of said first package portion is at least five times less than the specific gravity of said powdery dental component.

14. The device of claim 13 wherein the specific gravity of said foil pocket of said first package portion is at least eight times less than the specific gravity of said powdery dental component.

15. The device of claim 3 wherein the specific gravity of said foil bag is at least five times less than the specific gravity of said powdery dental component.

16. The device of claim 15 wherein the specific gravity of said foil bag is at least eight times less than the specific gravity of said powdery dental component.

* * * * *